United States Patent
Albertini et al.

[19]

[11] Patent Number: 6,116,077
[45] Date of Patent: Sep. 12, 2000

[54] CONSTRUCTION TEST APPARATUS

[75] Inventors: Carlo Albertini, Ispra, Italy; Mikhail Mogilevski, Novosibirsk, Russian Federation

[73] Assignee: European Community, Gasperi, Luxembourg

[21] Appl. No.: 09/113,801

[22] Filed: Jul. 10, 1998

Related U.S. Application Data

[63] Continuation of application No. PCT/EP96/04783, Oct. 30, 1996.

[30] Foreign Application Priority Data

Nov. 6, 1995 [EP] European Pat. Off. ............... 95307926

[51] Int. Cl.$^7$ ..................................................... G01M 7/00
[52] U.S. Cl. ............................................................ 73/12.05
[58] Field of Search .............................. 73/12.04, 12.06, 73/12.05, 12.09, 12.11

[56] References Cited

U.S. PATENT DOCUMENTS

| | | | |
|---|---|---|---|
| 3,831,441 | 8/1974 | Petty | 73/141 A |
| 4,133,201 | 1/1979 | Klinger | 73/12 |
| 4,161,874 | 7/1979 | Specker et al. | 73/12 |
| 5,325,701 | 7/1994 | Zilliacus | 73/12.04 |
| 5,487,298 | 1/1996 | Davis et al. | |

FOREIGN PATENT DOCUMENTS 2 696002  3/1994  France .

OTHER PUBLICATIONS

Derwent Publications Ltd., DATABASE WPI, London, GB; Section El, Week 9402, Class S02, AN 94–014838, XP002000768 & SU 1 783 329 A (Mosc Rail Eng Inst), Dec. 23, 1992.

*Primary Examiner*—William Oen
*Assistant Examiner*—Jewel V. Thompson
*Attorney, Agent, or Firm*—Pillsbury Madison & Sutro LLP

[57] ABSTRACT

Real scale investigations can be carried out on vehicle impacts using a vehicle, or part hereof, or crash barrier, tested on a large dynamic testing facility (LDTF). The LDTF includes nodes connected at either end of a sample under test crash barrier. The forces in the bar are measured by Hopkinson output bars connected at right angles at each node to measure perpendicular components of a force in the barrier. Vehicle may be equipped with additional instrumentation and used as an impactor against the barrier.

20 Claims, 5 Drawing Sheets

CONSTRUCTION TEST APPARATUS

This is a continuation of International Application No. PCT/EP96/04783 filed Oct. 30, 1996, which is designated the U.S.

This invention relates to improvements in or relating to construction or structure test apparatus and is more particularly, but not exclusively, concerned with "Hopkinson" bar systems used in crash-worthiness investigations of vehicles and road barriers.

Nowadays, about 50,000 people are killed per year in road accidents in Europe and thus improving energy absorbing systems in vehicles to dissipate impact energy incurred during a crash of the vehicle, for example with an obstacle, is very important. It is well known for automotive companies to carry out investigations on their vehicles with the aim of improving the safety characteristics of said vehicles. Due to the complexity of impact phenomena such investigations are generally carried out, by way of experiments on vehicles under crash conditions, on a real scale rather than investigating effects on scaled-down models. Consequently, such experiments tend to be expensive and are usually restricted by measuring the peak deceleration of a driver's mannequin and by analysis of the distribution of residual deformation. Experimental data received from existing load cells used as part of the testing apparatus tends to be severely complicated by wave effects incurred during an impact and such data is usually presented after some hardly substantiated filtering (particularly questionable in such measurements is the very essential value of a peak force).

However, wave propagation effects can instead of causing undesirable complications be utilised as a precise instrument for analysis of mechanical characteristics in dynamic loading when an appropriately equipped Hopkinson bar system is used. A Hopkinson bar is a popular apparatus used in the study of the dynamic response of materials. In essence, the Hopkinson bar is an elastic bar into which a known pressure-time loading applied at one end is propagated and, by suitable measurement techniques, details of the applied disturbance can be reconstructed. Usually, this will involve measuring signals from strain gauges at the input bar (which introduces a load to a sample being tested) and signals from an output, supporting bar to compute a force/displacement dependence in the sample (see in particular Lindholm U.S. 1971, High Strain Rate Tests, Techniques of Metal Research, Volume 5, part 1, J. Wiley). Measurable loading parameters (stress level, controlled value of deformation, velocity of deformation) are determinable respectively by the velocity of loading surface, the length of the bars and the permitted (elastic) stress in the bars. Hopkinson bar modifications are available for analysis of tension, compression, shear or torsional forces and so on. However, generally, Hopkinson bar systems are used for the study of mechanical properties of materials and experiments are conducted on rather small samples, for example several centimeters in length.

Nevertheless, experiments have been performed using a large dynamic test facility (LDTF) including a large Hopkinson bar installation used for investigating the dynamic behaviour of large specimens of heavy section reinforced concrete beams of about two to three meters in length. A paper entitled "Recent Development Results of LDTF Tests on Steel and Concrete Specimens" by C. Delzano, E. Gutierrez, P. M. Jones and G. Verzeletti presented in Nuclear Engineering and Design, 112 (1989), page 65 discusses a large (e.g. 200 meters) testing facility for the investigation of characteristics of concrete blocks but in quasi-static approach, without considering wave effects. This paper shows a 3-point bending Hopkinson bar system in which the force is measured at the input bar and displacements are measured by means of an optical system. However, very short output bars do not tend to permit accurate measurements to be produced according to Hopkinson bar theory therefore, analysis in said paper was made in quasi-static conditions. Even using two lang output bars in a 3-point bending scenario, standard Hopkinson bar measurements could only yield reliable information about forces in the case of precise symmetrical deformation (i.e. only at the initial stage of loading) because an intense plastic deformation (see FIG. 26 of the paper) will produce non-equal forces in perpendicular directions; non-controlled in a standard Hopkinson bar method.

French Patent Specification No. 2696002 shows a demonstration instrument for teaching purposes and is only concerned with measurements in a static system of 3d efforts or forces. The arrangement shown in 2696002 could not be used to measure impulsive forces because of stress wave reflections and inertia forces which tend to cause high levels of inaccuracy.

Furthermore the arrangement shown in 2696002 cannot be used on mechanical structures because its use requires modification of the structure being tested which changes the distribution of the efforts or forces in the structure itself. What is needed is an arrangement which leaves the original geometry of the structure being tested.

It is an object of the present invention to at least alleviate one of the aforementioned, or other, problems associated with testing of materials or mechanical structures or to provide a Hopkinson or pressure bar system for carrying out such testing which is improved in at least some respect.

According to the present invention there is provided a Hopkinson bar system or pressure bar system comprising a plurality of output bars arranged, in use, (preferably at an angle to one another) to measure components of an impulsive force in a sample or structure being tested.

Further according to the present invention there is provided a Hopkinson bar system or pressure bar system comprising at least two output bars operatively connected at an angle to one another (usually at right angles) by means of a node, said node, in use, being operatively connected to a sample or structure being tested.

In use, the sample may comprise a bar of about 2 or 3 meters long and may be attached e.g. by welding or by a force fit to one face of the node (usually of generally square section). The cross section of the node may be larger than that of the sample bar.

One of the output bars (usually at right angles to the sample bar) may comprise a collar embracing the node and there may be gaps defined between the node and the collar on opposed sides thereof permitting a small displacement of the node in a plane perpendicular to the other output bar (which bar may be axially aligned with the sample bar and attached to an opposing face of the node).

Preferably, low friction contact surfaces are provided on contacting surfaces of the output bar/s and node and more particularly on the collar (where provided) and node.

Usually, the system will include strain gauges positioned on the output bars to measure wave effects.

The system may include three output bars and the sample or structure may be of a complex three dimensional form under dynamic loading rather than just a simple bar.

In one embodiment of the present invention, the sample is a linear structure and may be in a three-point bending arrangement possibly under a non-central normal impact loading. A node may be provided at each end of the linear structure with each node connected to two mutually perpendicular output bars, two of said output bars being parallel with the linear structure and said other two output bars being parallel to one another.

In a second embodiment of the present invention, the sample is a real part of a vehicle (e.g. vehicle bumper with supporting constructions) undergoing an oblique collision with a wall (Hopkinson pressure output bar) more particularly under high velocity impact (e.g. 20 to 40 $ms^{-1}$).

A further embodiment includes a road barrier as the sample and a vehicle as an impactor, said vehicle being fitted with instrumentation and nodes being provided at either end of the road barrier. The road barrier may be tested with an oblique collision with the vehicle.

In order to more easily provide a high velocity impact both the sample and impactor may be accelerated towards one another, preferably, by using prestressed cables.

Further according to the present invention there is provided a method of modifying a real scale Hopkinson bar system, said method comprising operatively connecting, by means of a node, a sample or structure under test to at least two (untied) output bars arranged perpendicularly to one another.

Preferably, there is a substantially frictionless connection between at least one of the output bars and the node.

Further according to the present invention there is provided a method of measuring the perpendicular components of a force in a sample or structure under test by a Hopkinson bar system or pressure bar system including strain gauges, by measuring forces in a Hopkinson bar operatively connected to and axially aligned with said sample or structure and by measuring forces in a Hopkinson bar operatively connected but arranged perpendicularly to the sample or structure.

Said method may include impacting the sample or structure with an obstacle or impactor up to a velocity of about 20 to 40 $ms^{-1}$. The impactor is, preferably, cylindrical. The impactor may be arranged to be deformable during the impact.

Advantageously, therefore, a real size sample can be tested and analysed under conditions of assymetrical loading or impact using an LDTF with a Hopkinson bar system in accordance with the present invention.

Further according to the present invention there is provided a Hopkinson bar system or pressure bar system comprising a plurality of output bars arranged, in use, to measure components of an impulsive force along whatever selected direction in a sample or structure being tested, avoiding measurement inaccuracies due to stress wave reflections and inertia effects.

Preferably, the output bars are, in use, coupled with a sample or structure being tested, without geometric modifications being made to the structure which could disturb distribution of impulsive forces to be measured.

Many advantageous features of the system or method will be apparent from the following description and drawings.

Embodiments of a Hopkinson bar system or pressure bar system in accordance with the present invention will now be described, by way of example only, with reference to the accompanying, much simplified schematic drawings in which:

FIG. 1 shows the general layout of a known three point bending large dynamic testing facility (LDTF) Hopkinson bar system;

FIG. 1A in a cross-section taken along the lines 1A–1A in FIG. 1.

Figures 1, 1A:
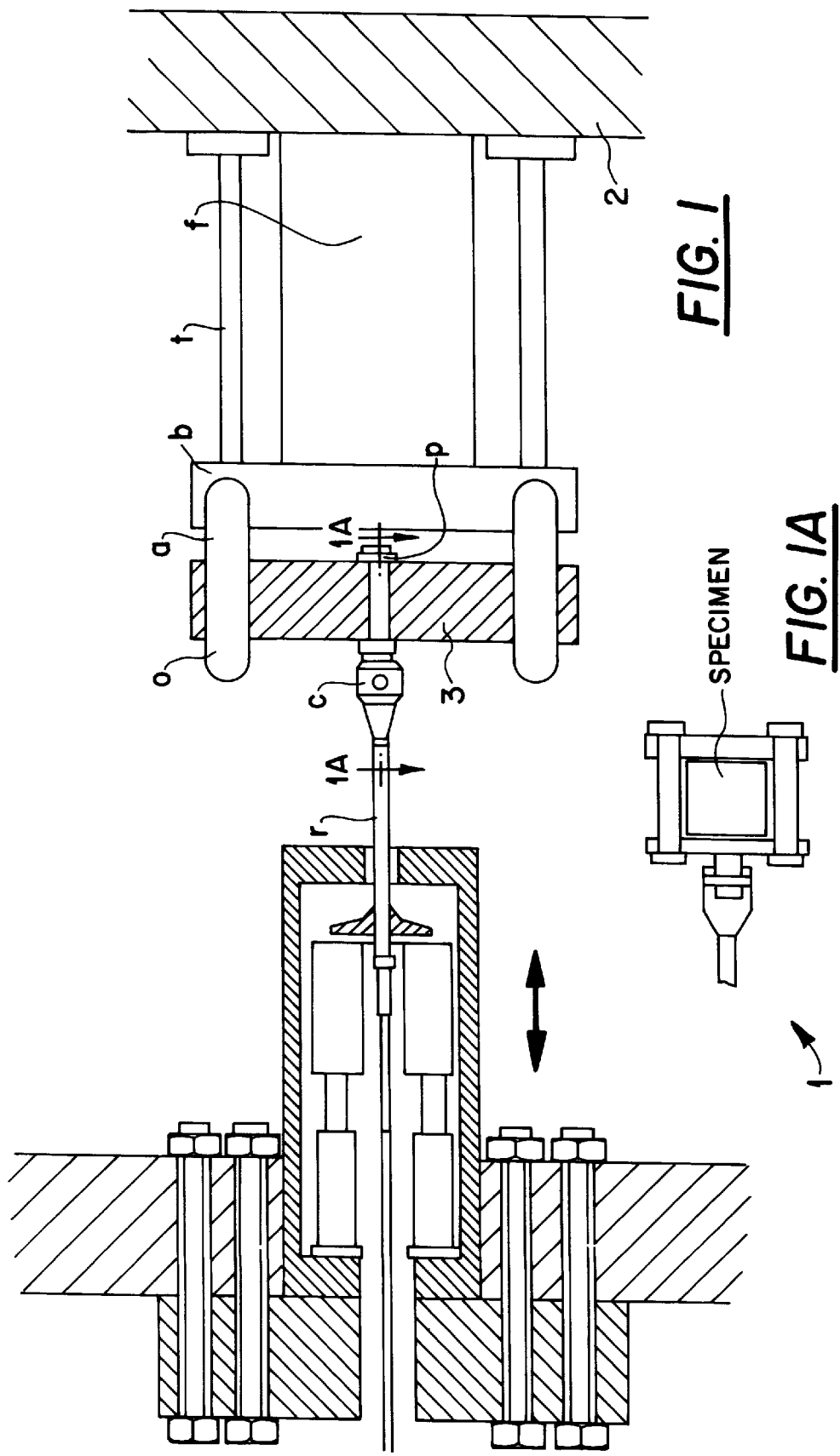

FIG. 1 of the drawings shows a three-point bending Hopkinson bar or pressure bar system which is basically known for the investigation of forces in reinforced concrete beams. Such equipment has been used in quasi-static conditions, without considering wave effects.

FIG. 1 shows an LDTF 1 comprising a support beam b fixed to a containing frame f. To increase flexible rigidity, beam b is anchored at each end to the apparatus foundation 2 by stiffening rods t. A sample or structure 3 under investigation is loaded by two rollers o which are connected to a support beam b through arms a and the attachment plate p, thus making up a three-point loading configuration. Impulse loading is applied through attachment plate p via the cleave c and the transmission rod r more particularly as explained in the aforementioned paper "Nuclear Engineering and Design 112 (1989) page 65".

Figure 2:
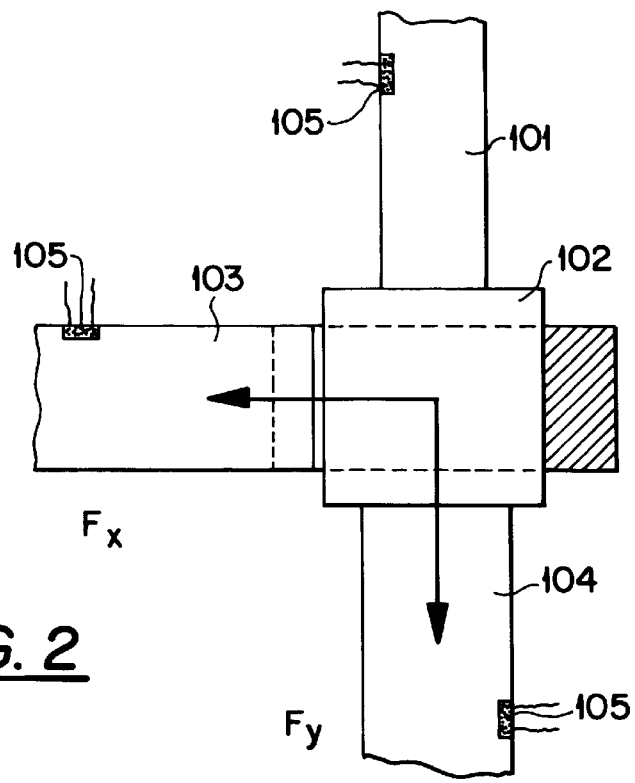
FIG. 2 shows details of a modification to the Hopkinson bar system shown in FIG. 1, said modification being in accordance with a first embodiment of the present invention.

The present invention is concerned with modifying, for example, the apparatus 1 as shown in FIG. 1, by the introduction of additional output bars arranged to measure perpendicular components of a force in a sample or structure under investigation and this may be done using the scheme as outlined in FIG. 2.

FIG. 2 illustrates how the Hopkinson bar system e.g. as outlined in FIG. 1 can be modified for measurement of components of a force at a controlled point.

Figure 3A:
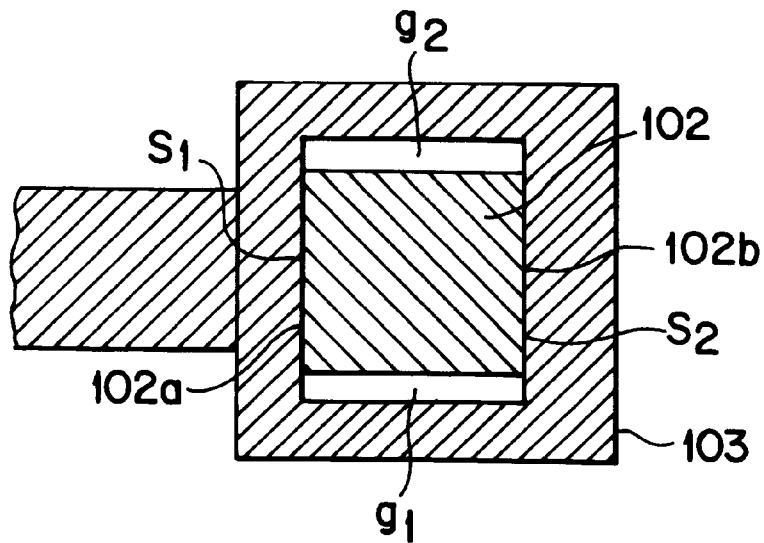
FIG. 3a shows a sectional view through a node taken on the line III—III of FIG. 2.

FIG. 2 shows part of a structure or sample 101 under investigation which is attached, for example, by gluing, welding or by a force-fit to a transient part or node 102 having a generally square cross-section (see FIGS. 3a and 3b) somewhat larger than the cross sections of the output bars 103, 104 for measuring perpendicular force components in the X and Y directions. Strain gauges 105 are positioned on the output bars 103 and 104 as well as on the structure part 101 under investigation. Structure part 101 may be under a generally axial load, in use, and may e.g. be part of a vehicle bumper acted upon by an impact bar (not shown). FIG. 3a shows a cross section through the node 102 which should be generally self-explanatory when viewed in conjunction with the perspective view 3b. It will be seen that the output bar 103 has a square section hollow ring collar 103a defining gaps $g_1$ and $g_2$ on either side of the node 102 permitting a small displacement of the node 102 relative to the output bar 103 in a plane perpendicular to output bar 104.

Low friction contact surfaces $s_1$ and $S_2$ are provided on opposite faces 102a, 102b of the node 102, which surfaces contact associated inner side walls 103b,103c of ring collar 103a.

The strain gauges 105 should be provided on sufficiently long output bars 103,104 and should receive values of stresses in given direction according to the formula:

$$\sigma_S = E\left[\frac{A}{A_S}\right]\epsilon_T$$

where E is the modulus of elasticity of pressure bars and $A/A_s$ is the area ratio between the pressure bars and sample under test, $\epsilon_T$ is the transmitted pulse and $o_s$ is the average stress in the sample (see pages 320 and 321 of Lindholm U.S. 1971, High Strain Rate Tests, Techniques of Metal Research, Volume 5, part 1, J Wiley, previously referred to).

In order to consider wave effects, rather long output bars are used to provide a desired time duration before wave reflection from the remote end, and accordingly the value of controlled deformation.

Figure 3B:
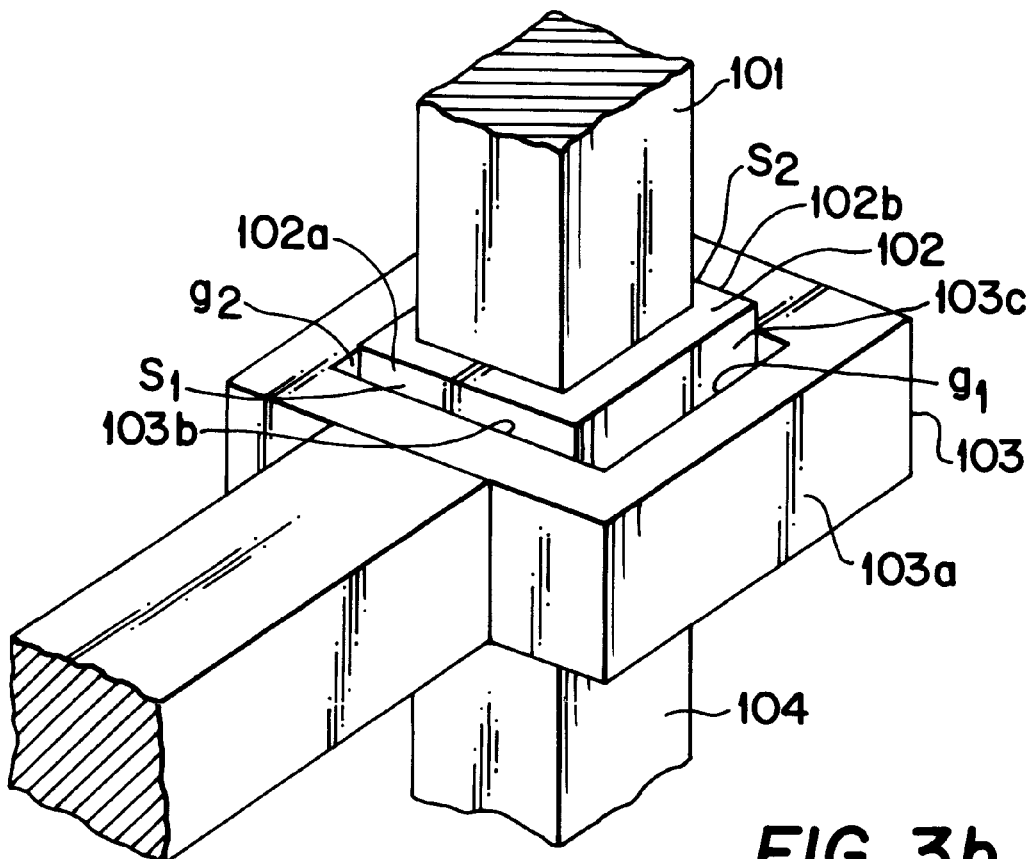
FIG. 3b shows a perspective view of the node drawn to a different scale.

Thus, the arrangement shown in FIGS. 2, 3a,3b allows the stress distribution in a Hopkinson bar system to be measured with independent measurement of all components of forces at control points in a sample under test, unlike in the Nuclear Engineering and Design, 112 (1989) paper previously referred to.

Even in the case of symmetrical loading of a complex structure, a loss of stability in some element can cause an intense local deformation followed by a drastic redistribution of forces. The arrangement shown in FIGS. 2, 3a, 3b can be used to measure perpendicular components of forces at controlled points of a structure using the two Hopkinson output bars 104,105.

Where, for example, complex three dimensional structures are under test, three Hopkinson output bars may be used. These could be employed mutually at right angles, e.g. at the same node. Each bar 104,105 does not impede the perpendicular displacements of the controlled node 102 and in practice does not influence measurements of other force components if virtually negligible friction is provided between the node 102 and contact surfaces (side walls 103b,103c).

The arrangement shown in FIG. 2 may be modified to investigate with precise measurements an extensive programme of crash impact phenomena at levels of a different complexity. A first characteristic scheme is shown in FIG. 4.

Figure 5:
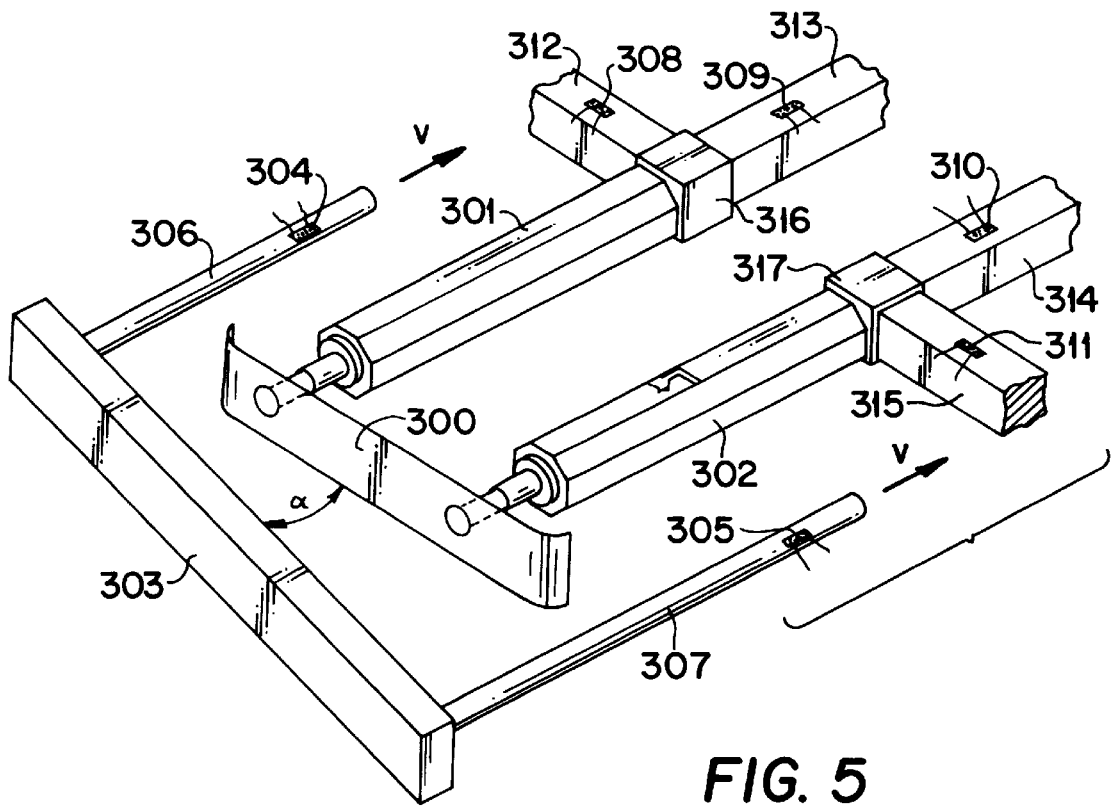
FIG. 5 shows a scheme for investigating an oblique collision of a deformable safety construction with a rigid wall, in accordance with the a third embodiment of present invention.
Figure 6:
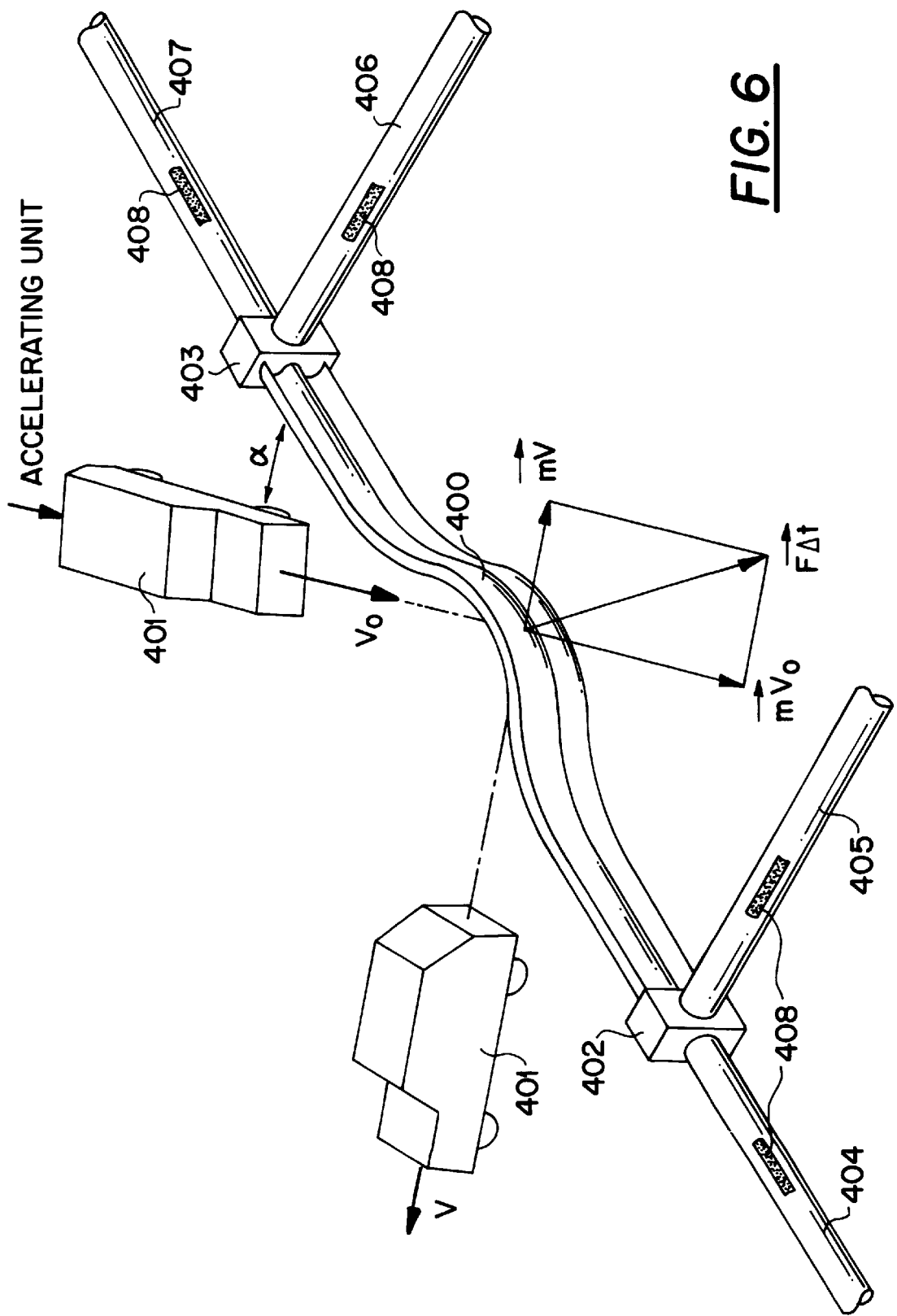
FIG. 6 shows a real-size experiment with a road barrier and a vehicle, in accordance with a fourth embodiment of the present invention.

Further characteristic schemes are shown in FIGS. 5 and 6.

The primary, basic level of investigation includes testing of linear structures (for example, a rod, a profile, a tube, a part of a real road barrier with poles or a real bumper) in cases of symmetrical axial impact loading (a typical 3-point bending). FIG. 4 shows a scheme in which the effect of a non-central normal impact is investigated.

Figure 4:
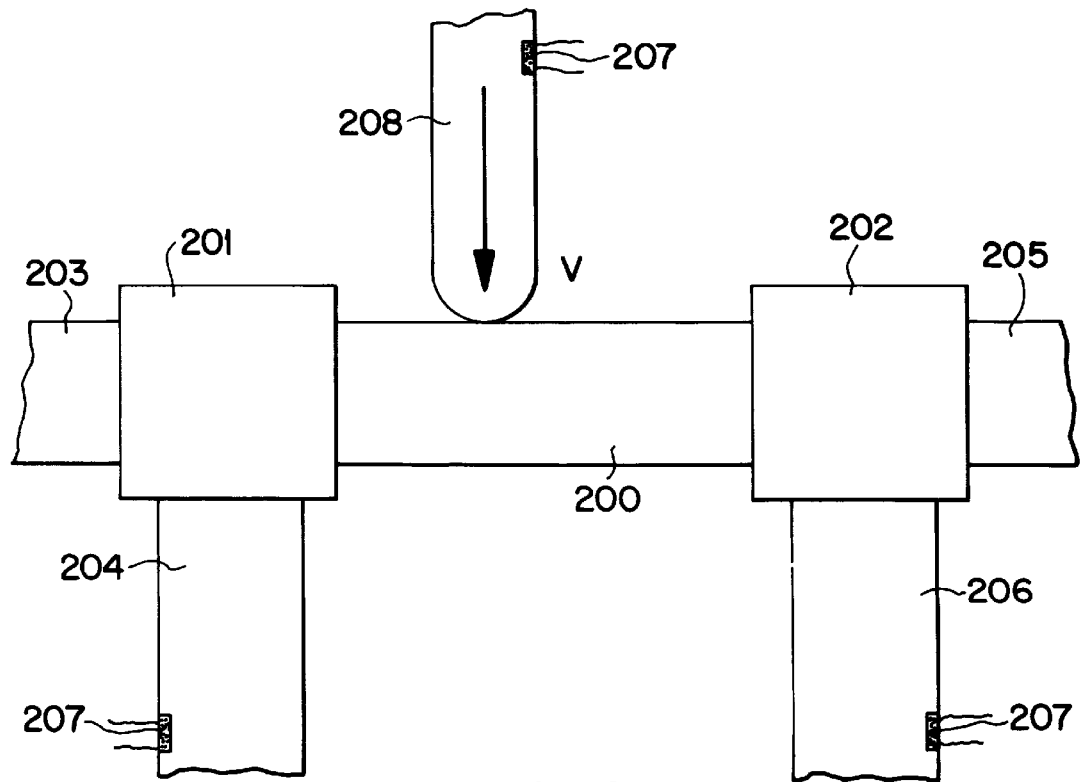
FIG. 4 shows a scheme in accordance with a second embodiment of the present invention for investigating a non-central normal loading of a linear structure.

FIG. 4 shows a sample or structure 200 under test which is connected at either end to a node 201,202, said nodes being connected in turn to associated Hopkinson output bars 203,204,205,206 in the manner shown schematically. Thus, output bar 203 is at right angles to output bar 204 and output bar 205 is at right angles to output bar 206. Once again, the nodes 201,202 may be connected to the sample 200 by welding or otherwise and low or negligible friction should be provided between each node 201,202 and respective contact surfaces of the output bars 203,204,205 and 206. Each node 201,202 and connection with associated output bars 203,204,205,206 may be of the detailed form shown in FIG. 3b with, for example, the output bar 204 or 206 replacing output bar 105. Strain gauges 207 are provided on the output bars 203,204,205,206 (FIG. 4 shows strain gauges on output bars 203,205) and also on an incident or impact bar 208 (a driver) which, in use, provides a non-central normal impact on the sample 200 under test.

FIG. 5 illustrates a scheme for investigation of an oblique collision of a deformable vehicle safety construction in the form of a real size car bumper 300 with supporting deformable constructions or elements 301,302 with a rigid wall 303. The arrangement shown in FIG. 5 represents a second level of complexity corresponding to investigations of the mechanical characteristics of 2 or 3 dimensional model structures representing the energy absorbing parts of vehicles of which the real bumper 300 and supporting constructions 301,302 are an example. It is envisaged that an oblique collision (bumper 300 is arranged at the angle a to the rigid wall 303—forming part of a Hopkinson bar arrangement) will take place in conditions of high velocity impact and other typical rigid obstacles for example, a wall or a column, could be investigated. FIG. 5 shows strain gauges 304,305 attached to instrumented impact Hopkinson bars or rods 306,307 connected in parallel relationship at either end of the rigid wall 303. Additional strain gauges 308,309,310,311 are provided on associated Hopkinson output bars 312,313,314 and 315 connected at nodes 316 and 317 in a similar manner to that previously described.

A further or third level of complexity is illustrated in FIG. 6 which depicts a real size experiment with a road barrier 400 and a vehicle 401. FIG. 6 illustrates a real case scenario of mutual simultaneous deformation of the vehicle 401 and the obstacle 400 in a high velocity impact. It is possible to measure mechanical characteristics in the case of the oblique collision of the car 401 with real road barrier 400 with different variants of cars and different angles of impact with particular designs of barrier. Thus the vehicle 401 may be equipped with instrumentation and driven at the road barrier 400 (sample under the test) at a velocity $V_O$ with the vehicle bouncing off the deformed barrier 400 at the velocity V as shown in FIG. 6. Nodes 402 and 403 are provided at either end of the road barrier 400, for example in the manner as previously described, said nodes 402,403 being connected to Hopkinson output bars 404,405,406,407 equipped with strain gauges 408 from which it is possible to estimate a mean force from impulse conservation law as shown diagrammatically on the FIGURE.

Figure 7:
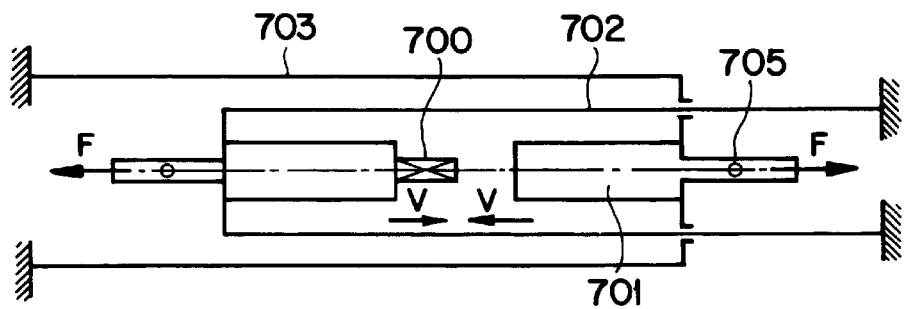
FIG. 7 shows a scheme with movement of a driver and a sample in accordance with a fifth embodiment of the present invention.

FIG. 7 illustrates a further possible scheme so that a level of impact velocity higher than 20 meters per second can be provided for heavy constructions under investigation. The scheme illustrated in FIG. 7 includes a sample or structure 700 under investigation and an impactor 701 (moving obstacle with attached output bar). Two prestressed cables 702,703 are utilised to accelerate both the sample 700 and impactor 701 towards one another (when released or fired towards one another) rather than accelerating only the impactor towards a sample as in previous arrangements. Numeral 705 represents an explosive bolt. The acceleration of both the impactor 701 and sample 700 requires essentially less energy. With colliding bodies of equal mass the total kinetic energy of the two bodies at the same relative velocity may be double that of one accelerated body. The excess of energy in the case of one accelerated body is sent to the movement of the centre of masses. The second advantage of the encounter movement of a sample and an obstacle resides in a more compact and reliable installation being feasible, which installation requires no special attachment to stop the system after collision.

Thus, embodiments of the present invention provide facility in a 1:1 scale experiment on a complex structure (for example real vehicle part or barrier) for detail information of distribution of forces and displacements during the process of a crash impact with velocities up to about 20 to 40 meters per second. Such information is required for developing effective safety systems for different vehicles and road barriers.

Measurement inaccuracies due to stress waves reflections (such as occur in French Patent Specification No. 2696002) may be alleviated in the present invention by any of the following:

(1) proportioning the bar length to the test pulse duration; i.e. long pulse duration=long bars or installation at the bar end of a stress wave trap (stress wave absorber);

(2) proportioning the bar diameter (thickness) to the bar length in a way that non-axial elastic stress waves can propagate in the bars without disturbances from lateral oscillations of the bars;

(3) matching as near as possible the mechanical impedance pAC of the test sample and of the bars; p is density, A cross section and C elastic stress wave speed.

It is to be understood that the scope of the present invention is not to be unduly limited by the particular choice of terminology and that a specific term may be replaced or supplemented by any equivalent or generic term. Further it is to be understood that individual features, method, theory or functions related to the Hopkinson bar system or parts thereof, alone or in combination might be individually patentably inventive. The singular may include the plural or vice versa. In particular, any disclosure in this specification of a range for a variable or parameter shall be taken to include a disclosure of any selectable or derivable subrange within that range and shall be taken to include a disclosure of any value for the variable or parameter found within or at an end of the range.

What is claimed is:

1. A Hopkinson bar system for measuring components of an impulsive force in a sample or structure comprising a plurality of output bars connected and arranged, in use, to measure said force components, said force components being measured by a strain gauge bonded to the Hopkinson Bar system.

2. A system as claimed in claim 1 in which the output bars are arranged, in use, at an angle to one another.

3. A system as claimed in claim 1 in which the output bars are, in use, coupled with a sample or structure being tested, without geometric modifications being made to the structure which could disturb distribution of impulsive forces to be measured.

4. A Hopkinson bar system for measuring components of an impulsive force in a sample or structure comprising at least two output bars operatively connected at an angle to one another by means of a node, said node, in use, being operatively connected to said sample or structure.

5. A system as claimed in claim 4 dimensioned to test a sample in the form of a bar of about 2 or 3 meter long.

6. A system as claimed in claim 5 in which the sample is connected, in use, to one face of the node.

7. A system as claimed in claim 4 in which the cross section of the node is larger than that of the sample.

8. A system as claimed in claim 4 in which one of the output bars comprises a collar embracing the node, gaps defined between the node and the collar on opposed sides thereof, said gaps configured to permit a small displacement of the node in a plane perpendicular to the other output bar, said bar being axially aligned with the sample and attached to an opposing face of the node.

9. A system as claimed in claim 4 having low friction contact surfaces on at least one of the output bars provided on contacting surfaces on at least one of the output bars and node.

10. A system as claimed in claim 4 in which the sample is a linear structure, in a three-point bending arrangement, under a non-central normal impact loading; a node being provided at each end of the linear structure with each node connected to two mutually perpendicular output bars, two of said output bars being parallel or axially aligned with the linear structure and said other two output bars being parallel to one another.

11. A system as claimed in claim 4 in which the sample is a real part of a vehicle undergoing an oblique collision with a wall under a high velocity impact.

12. A system as claimed in claim 11 in which the high velocity impact is between 20 to 40 $ms^{-1}$.

13. A system as claimed in claim 4 in which a road barrier is the sample and a vehicle is provided as an impactor, said vehicle being fitted with instrumentation and nodes being provided at either end of the road barrier.

14. A system as claimed in claim 4 in which a high velocity impact is provided by the sample or the impactor being accelerated towards one another by using prestressed cables.

15. A system as claimed in claim 4 including three output bars, said output bars being mutually at right angles.

16. A system as claimed in claim 15 in which said three output bars are at right angles to one another.

17. A system as claimed in claim 4 in which said at least two output bars are operatively connected at right angles to one another.

18. A Hopkinson bar system for measuring components of an impulsive force in a sample or structure comprising a plurality of output bars arranged, in use, to measure said components along whatever selected direction in said sample or structure, avoiding measurement inaccuracies due to stress wave reflections and inertial affects.

19. A method of modifying a real scale Hopkinson bar system, said method comprising operatively connecting, by means of a node, a sample or structure under test to at least two untied output bars, arranging said output bars perpendicularly to one another and providing a substantially frictionless connection between at least one of the output bars and the node.

20. A method of measuring the perpendicular components of a force in a sample or structure under test by a Hopkinson bars system or pressure bar system including strain gauges, by measuring forces in a Hopkinson bar operatively connected to and axially aligned with said sample or structure and by measuring forces in a Hopkinson bar operatively connected but arranged perpendicularly to the sample or structure, said method including impacting the sample or structure with an obstacle or impactor up to a velocity of about 20 to 40 $ms^{-1}$.

* * * * *